United States Patent [19]
Ao et al.

[11] Patent Number: 5,861,522
[45] Date of Patent: Jan. 19, 1999

[54] PRODUCTION OF BRIDGED METALLOCENE COMPLEXES AND INTERMEDIATES THEREFOR

[75] Inventors: Meng-Sheng Ao; Hassan Y. Elnagar; Arcelio J. Malcolm; Jamie R. Strickler; Ronny W. Lin; John F. Balhoff, all of Baton Rouge, La.

[73] Assignee: Albemarle Corporation, Richmond, Va.

[21] Appl. No.: 853,698

[22] Filed: May 8, 1997

Related U.S. Application Data

[63] Continuation-in-part of Ser. No. 672,128, Jun. 27, 1996, Pat. No. 5,710,299.
[51] Int. Cl.$^6$ .............................. C07F 17/00; C07F 7/00
[52] U.S. Cl. ................... 556/11; 556/12; 556/43; 556/47; 556/53; 526/160; 526/943; 502/103; 502/117
[58] Field of Search .................. 556/11, 12, 43, 556/47, 53; 526/943, 160; 502/103, 117

[56] References Cited

U.S. PATENT DOCUMENTS

| | | | |
|---|---|---|---|
| 4,528,408 | 7/1985 | Plummer | 568/808 |
| 4,794,096 | 12/1988 | Ewen | 502/117 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,120,867 | 6/1992 | Welborn, Jr. | 556/12 |
| 5,145,819 | 9/1992 | Winter et al. | 502/117 |
| 5,296,434 | 3/1994 | Karl et al. | 502/117 |
| 5,314,973 | 5/1994 | Welborn, Jr. | 526/126 |
| 5,324,800 | 6/1994 | Welborn, Jr. et al. | 526/160 |
| 5,329,033 | 7/1994 | Spaleck et al. | 556/53 |
| 5,441,920 | 8/1995 | Welborn, Jr. | 502/103 |
| 5,455,365 | 10/1995 | Winter et al. | 556/7 |
| 5,455,366 | 10/1995 | Rohrmann et al. | 556/8 |
| 5,512,693 | 4/1996 | Rosen et al. | 556/7 |
| 5,532,396 | 7/1996 | Winter et al. | 556/11 |
| 5,541,350 | 7/1996 | Murata et al. | 556/10 |
| 5,556,997 | 9/1996 | Strickler et al. | 556/11 |
| 5,569,746 | 10/1996 | Lee et al. | 534/11 |
| 5,585,508 | 12/1996 | Kuber et al. | 556/11 |

FOREIGN PATENT DOCUMENTS

| | | |
|---|---|---|
| 2055218 | 5/1992 | Canada . |
| 2084016 | 5/1993 | Canada . |
| 2084017 | 5/1993 | Canada . |
| 0530908 | 3/1993 | European Pat. Off. . |
| 0549900 | 7/1993 | European Pat. Off. . |
| 0581754 | 2/1994 | European Pat. Off. . |
| 05659757 | 6/1995 | European Pat. Off. . |
| 4434640 | 2/1996 | Germany . |
| 6345809 | 12/1994 | Japan . |
| 8208733 | 8/1996 | Japan . |
| 646438 | 11/1984 | Switzerland . |

OTHER PUBLICATIONS

Ray and Westland; "The Infrared Spectra of Some Compounds of Zirconium(IV) and Hafnium(IV) Tetrahalides and Ligands Containing Group V Donor Atoms"; Inorganic Chemistry, vol. 4, No. 10, Oct. 1965, pp. 1501–1504.
Morrison and Boyd, 3rd Edition, Chapter 19, p. 630 and p. 636 (1976).
Spalek, et al., The Influence of Aromatic Substituents on the Polymerization Behavior of Bridged Zirconocene Catalysts; Organometallics, vol. 13, No. 3, 1994, pp. 954–963.
Spalek, et al., "High Molecular Weight Polypropylene through Specifically Designed Zirconocene Catalysts"; Angew Chem. Int. Ed. Engl, 1992, vol. 31, No. 10, pp. 1347–1350.
Jordan, et al., "Synthesis and Structures of Neutral and Cationic rac–(Ethylenebis(tetrahydroindenyl))zirconium(IV) Benzyl Complexes"; Organometallics, vol. 9, No. 5, 1990, pp. 1539–1545.
Samuel et al; "π–Cyclopentadienyl and π–Indenyl Compounds of Titanium, Zirconium, and Hafnium Containing σ–Bonded Organic Substituents"; Journal of the American Chemical Society, 1973, 95:19; pp. 6263–6267.
The Metallocene Monitor, Special Feature; Exxon, Hoechst, and BASF All Have Parts of Metallocene–Catalyzed Isotactic PP; pp. 4–10; (undated).
Stehling, et al., "ansa–Zirconocene Polymerization Catalysts with Annelated Ring Ligands–Effects on Catalytic Activity and Polymer Chain Length"; Organometallics, 1994, vol. 13, No. 3, pp. 964–970.
Foster et al., "Highly Stable Catalysts For The Stereospecific Polymerization of Styrene", Organometallics, 1996, vol. 15, pp. 2404–2409.
Foster et al., "Aromatic Substituted Group 4 Metallocene Catalysts for the Polymerization of α–Olefins", Organometallics, 1996, vol. 15, pp. 4951–4953.

*Primary Examiner*—Porfirio Nazario-Gonzalez
*Attorney, Agent, or Firm*—Philip M. Pippenger

[57] ABSTRACT

Bridged metallocene compounds are produced by a process of promising commercial utility for plant-sized operations. One of the key steps of the process involves converting a deprotonated silicon-, germanium- or tin-containing ligand into the metallocene. Preferably, and in accordance with an embodiment of the invention, this is accomplished to great advantage by adding a diamine adduct of a Group IV, V, or VI metal tetrahalide to a solution or slurry formed from a deprotonated silicon-, germanium- or tin-containing ligand and an organic liquid medium so as to form a metallocene. The overall process of the invention involves the direct conversion of benzoindanones to benzoindanols which, without isolation, are converted to benzoindenes. Thereupon the benzoindenes are bridged by deprotonating the benzoindenes with a strong base such as butyllithium and reacting the resultant deprotonated product with a suitable silicon-, germanium- or tin-containing bridging reactant such as dichlorodimethylsilane. The resultant bridged product is deprotonated with a strong base such as butyllithium and reacted with a suitable Group IV, V, or VI metal-containing reactant such as $ZrCl_4$ to provide a silicon-, germanium- or tin-bridged Group IV, V, or VI metal complex, such as a dihydrocarbylsilyl-bridged zirconocene complex.

30 Claims, No Drawings

PRODUCTION OF BRIDGED METALLOCENE COMPLEXES AND INTERMEDIATES THEREFOR

REFERENCE TO RELATED APPLICATION

This is a continuation-in-part of prior patent application, Ser. No. 08/672,128, filed Jun. 27, 1996, now U.S. Pat. No. 5,710,299.

TECHNICAL FIELD

This invention relates to a new, efficacious process for producing bridged metallocene complexes, such as for example dihydrocarbylsilyl-bridged zirconocene complexes, and for producing key intermediates used in the overall synthesis process.

BACKGROUND

The synthesis of certain dihydrocarbylsilyl-bridged zirconocene complexes and their use as polymerization catalyst components have been reported heretofore. See for example U. Stehling et al., *Organometallics* 1994, 13, 964–970. Rohrmann et al. U.S. Pat. No. 5,455,366 issued Oct. 3, 1995, describes multistep processes for producing a variety of metallocenes having benzo-fused indenyl derivatives as ligands. These materials are also shown to have utility in the formulation of polymerization catalysts.

While workable, these prior processes are deemed best suited for laboratory-scale operations. Thus a need exists for a simplified process which can be used to make desired bridged metallocenes, such as dihydrocarbylsilyl-bridged zirconocene complexes, in acceptable yields in large scale production facilities. One of the key steps in any such process is the interaction between a protonated bridged ligand and a metal tetrahalide salt to form the desired bridged metallocene. Unfortunately, this reaction tends to be tedious, difficult and time-consuming.

SUMMARY OF THE INVENTION

This invention provides, inter alia, a new process for producing bridged metallocene compounds—such as are described in the foregoing Rohrmann et al. patent—which is both efficacious and of promising commercial utility in plant-sized operations.

One of the key steps of the process involves converting a deprotonated silicon-, germanium- or tin-containing ligand into the metallocene. Preferably, and in accordance with an embodiment of the invention, this is accomplished to great advantage by adding a diamine adduct of a Group IV, V, or VI metal tetrahalide to a solution or slurry formed from a deprotonated silicon-, germanium- or tin-containing ligand and an organic liquid medium so as to form a metallocene. As will be seen hereinafter, significant advantages can be realized by conducting this step in this manner.

The overall process of the invention, which constitutes another embodiment of this invention, involves the direct conversion of benzoindanones to benzoindanols which, without isolation, are converted to benzoindenes. Thereupon the benzoindenes are bridged by deprotonating the benzoindenes with a strong base such as butyllithium and reacting the resultant deprotonated product with a suitable silicon-, germanium- or tin-containing bridging reactant such as dichlorodimethylsilane. The resultant bridged product is deprotonated with a strong base such as butyllithium and reacted with a suitable Group IV, V, or VI metal-containing reactant such as $ZrCl_4$ to provide a silicon-, germanium- or tin-bridged Group IV, V, or VI metal complex, such as a dihydrocarbylsilyl-bridged zirconocene complex. In this embodiment, this last step can be conducted in various ways but preferably is conducted by adding a diamine adduct of a Group IV, V, or VI metal tetrahalide to a solution or slurry formed from a deprotonated silicon-, germanium- or tin-containing ligand and an organic liquid medium so as to form a metallocene.

Unlike the Rohrmann et al. procedures, the overall processes of this invention involve the direct conversion of benzoindanones to benzoindanols which, without isolation, in turn are converted to benzoindenes. Thereupon the benzoindenes are bridged by deprotonating the benzoindenes with a strong base such as butyllithium and reacting the resultant deprotonated product with a suitable silicon-, germanium- or tin-containing bridging reactant. The resultant bridged product so formed is then deprotonated with a strong base such as butyllithium and reacted with a suitable Group IV, V, or VI (formerly known as Groups IVb, Vb and VIb) metal-containing reactant to provide a silicon-, germanium- or tin-bridged Group IV, V, or VI metal complex, such as a dihydrocarbylsilyl-bridged zirconocene complex. The invention thus provides, inter alia, a straightforward commercially feasible sequence of operations. Moreover, the initial benzoindanones used in the practice of such sequence can be formed readily and in high yield by reaction of a 2-haloacyl halide with naphthalenes unsubstituted in at least the 1-and 2-positions. This reaction normally produces a mixture of two isomers, namely a 4,5-benzoindan-1-one as the major isomer and a 4,5-benzoindan-3-one as the minor isomer. These isomers can, if desired, be separated from each other by known procedures. Thus unless expressly stated otherwise, the term 4,5-benzoindanone as used herein refers to at least one 4,5-benzoindan-1-one or at least one 4,5-benzoindan-3-one, or a mixture of at least one 4,5-benzoindan-1-one and at least one 4,5-benzoindan-3-one. Similarly depending on the isomeric makeup of the initial 4,5-benzoindanone(s), the conversion of a 4,5-benzoindanone to a 4,5-benzoindanol can form one or more 4,5-benzoindan-1-ols or one or more 4,5-benzoindan-3-ols, or a mixture of one or more 4,5-benzoindan-1-ols and one or more 4,5-benzoindan-3-ols. Thus unless expressly stated otherwise, the term 4,5-benzoindanol as used herein refers to at least one 4,5-benzoindan-1-ol or at least one 4,5-benzoindan-3-ol, or a mixture of at least one 4,5-benzoindan-1-ol and at least one 4,5-benzoindan-3-ol.

The above and other embodiments will become still further apparent from the ensuing description and appended claims.

FURTHER DETAILED DESCRIPTION OF THE INVENTION

In one of its embodiments this invention provides a process of forming a 4,5-benzoindanol which comprises mixing together at least one of each of the following: (a) a 4,5-benzoindanone, (b) an alkali or alkaline earth metal borohydride or alkali or alkaline earth metal aluminum hydride, and (c) a hydroxyl-containing compound capable of interacting with (b) to serve as a hydrogen source, such that a 4,5-benzoindanol is formed. Such borohydride or aluminum hydride reductions of the carbonyl group can be conducted with high selectivity and in good yields. The operation is preferably conducted in a liquid ether reaction medium such as tetrahydrofuran and alkyltetrahydrofurans.

The preferred 4,5-benzoindanones for use in the process are 4,5-benzoindan-1-ones or mixtures of a major molar proportion of one or more 4,5-benzoindan-1-ones and a minor molar proportion of one or more 4,5-benzoindan-3-ones, such as for example a mixture of about 90 mol % of a 4,5-benzoindan-1-one and about 10 mol % of a 4,5-benzoindan-3-one.

Sodium borohydride is the preferred reducing agent, but use can be made of other compounds such as sodium aluminum tetrahydride, sodium aluminum hexahydride, and their lithium or potassium analogs. Generally speaking, the alkali metal derivatives are preferred over the alkaline earth compounds, and as compared to the hexahydrides, the tetrahydrides are the more preferred reagents, especially the borohydrides. Such more preferred reagents may thus be depicted by the formula $AMH_x(OR)_y$ wherein A is an alkali metal, M is boron or aluminum, R is hydrocarbyl, x is an integer in the range of 2 to 4, and y is an integer in the range of 0 to 2, the sum of x and y being 4. Most preferably y is zero and M is boron.

The hydroxyl-containing component used in the reaction as a source of hydrogen is either water or a suitable hydroxyorganic compound such as an alcohol, a polyol, or a phenol. Water or lower alkanols or mixtures thereof are preferred.

The 4,5-benzoindanones used in this reaction are illustrated by formula (A) below which for convenience depicts the 4,5-benzoindan-1-ones. The 4,5-benzoindan-3-ones have the same formula except that the keto functionality is in the 3-position of the 5-membered ring instead of the 1-position as shown.

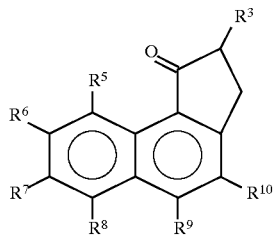

(A)

where $R^3$ and $R^5$ through $R^{10}$ are the same or different and are a hydrogen atom; a halogen atom (preferably a fluorine, chlorine or bromine atom); a hydrocarbyl group containing up to about 10 carbon atoms each (e.g., a $C_1$ to $C_{10}$, and preferably a $C_1$ to $C_4$ alkyl group, a $C_6$ to $C_{10}$ aryl group, a $C_3$ to $C_{10}$ cycloalkyl group, a $C_2$ to $C_{10}$, and preferably a $C_2$ to $C_4$ alkenyl group, a $C_7$ to $C_{10}$ aralkyl group, etc.); a halohydrocarbyl group containing up to about 10 carbon atoms and up to about 3 halogen atoms each; an —$NR_2$, —SR, —$OSiR_3$, —$SiR_3$, or —$PR_2$ group in which R is a hydrocarbyl group containing up to about 10 carbon atoms. In preferred embodiments $R^3$ is an alkyl group, most preferably a methyl group, and at least four and most preferably all six of $R^5$ through $R^{10}$ are hydrogen atoms.

The 4,5-benzoindanols formed in this reaction likewise can exist in either of two isomeric forms derived from the isomeric forms of the 4,5-benzoindanone(s) used as the starting material. Such 4,5-benzoindanols are thus illustrated by formula (B) below which depicts the 4,5-benzoindan-1-ols. The 4,5-benzoindan-3-ols have the same formula except that the hydroxyl group is in the 3-position of the 5-membered ring instead of the 1-position as shown.

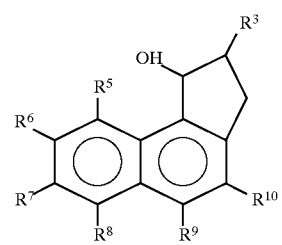

(B)

where $R^3$ and $R^5$ through $R^{10}$ are as described above.

Another embodiment of this invention is the process of forming 4,5-benzoindene which comprises reducing a 4,5-benzoindanone to a 4,5-benzoindanol as described above, and catalytically dehydrating the 4,5-benzoindanol (Formula (B) above) so formed. The 4,5-benzoindenes formed in this reaction can be depicted by the formula:

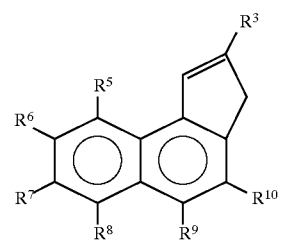

(C)

where $R^3$ and $R^5$ through $R^{10}$ are as described above. Formula (C) depicts an isomer having a double bond of the 5-membered ring in the 1-position. In another isomer that double bond can instead be in the 2-position, and mixtures of these respective isomers can be formed.

The preferred method of effecting the dehydration step involves use of an arylsulfonic acid catalyst such as p-toluenesulfonic acid. In conducting this reaction sequence the reduction of the benzoindanone (Formula (A) above) to the benzoindanol (Formula (B) above) is preferably terminated by quenching the reaction mixture with water or a suitable aqueous solution or mixture, and separating off the aqueous phase before proceeding with the catalytic dehydration reaction. By conducting the reduction step in a low boiling ether reaction medium such as tetrahydrofuran, the separations after the aqueous quench can be readily accomplished by extracting the quenched reaction mixture with a liquid hydrocarbon, preferably a mononuclear aromatic hydrocarbon such as toluene or xylene, having a higher boiling point or higher initial boiling point than the ether, and distilling at least the ether from the resultant extract. Use of an excess of the hydrocarbon provides, on completion of the distillation, a suitable predominately hydrocarbonaceous reaction medium in which to conduct the dehydration step. Moreover on completion of the dehydration, the water formed during the dehydration plus residual water, if any, from the quenching step, can be readily removed by azeotropic distillation. While the catalytic dehydration is best carried out using an arylsulfonic acid catalyst, other ways of performing the dehydration can be used especially for laboratory scale operations. Such methods include use of oxalic acid as dehydration catalyst or reaction of the benzoindanol with dehydrating substances such as magnesium sulfate or molecular sieves. For references describing such alternative albeit far less desirable procedures, see Rohrmann et al. at Column 9, lines 41–43.

In summary therefore, a preferred process sequence per this invention for converting a 4,5-benzoindanone to a 4,5-benzoindene comprises: (a) a 4,5-benzoindanone is reduced to a 4,5-benzoindanol in an ether-containing reaction medium by use of an alkali metal borohydride and water or an alcohol or a mixture thereof; (b) the reduction is terminated by quenching the reaction mixture with a suitably large amount of water (or appropriate aqueous mixture); (c) a separation is made between the water and organic constituents of the reaction mixture, by extracting the quenched reaction mixture with a liquid hydrocarbon having a higher boiling point or higher initial boiling point than the ether, and, if present, the alcohol; (d) distilling off said ether and, if present, the alcohol to leave a liquid hydrocarbon solution of the 4,5-benzoindanol; (e) catalytically dehydrating 4,5-benzoindanol so formed to the corresponding 4,5-benzoindene while in liquid hydrocarbon solution, and (f) removing water from the dehydration reaction mixture by azeotropic distillation. In this embodiment it is especially preferred that in Formulas (A), (B) and (C) above, $R^3$ be an alkyl group, most preferably a methyl group, and that at least four and most preferably all six of $R^5$ through $R^{10}$ be hydrogen atoms.

Another embodiment of this invention comprises converting the 4,5-benzoindenes (Formula C above) to a silicon-, germanium- or tin-bridged complex of the formula:

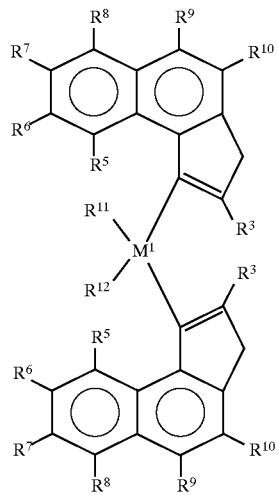

(D)

where $R^3$ and $R^5$ through $R^{10}$ are as described above, $M^1$ is a silicon, germanium or tin atom (preferably a silicon atom), and $R^{11}$ and $R^{12}$ are the same or different and are a hydrocarbyl group containing up to about 18 carbon atoms each (e.g., a $C_1$ to $C_{18}$, and preferably a $C_1$ to $C_4$ alkyl group, a $C_6$ to $C_{18}$ aryl group, a $C_3$ to $C_{18}$ cycloalkyl group, a $C_2$ to $C_{18}$, and preferably a $C_2$ to $C_4$ alkenyl group, a $C_7$ to $C_{18}$ aralkyl group, etc.); or a hydrocarbyl(oxyalkylene) or hydrocarbylpoly(oxyalkylene) group containing up to about 100 carbon atoms (preferably where the oxyalkylene moiety or moieties are oxyethylene and or oxymethylethylene, and in the case of long chain polyoxyalkylenes, the oxyalkylene moieties are in random or block arrangements. Most preferably, $M^1$ is a silicon atom; $R^{11}$ and $R^{12}$ are the same and are $C_1$ to $C_4$ alkyl groups, most preferably methyl or ethyl groups, $R^3$ is an alkyl group, most preferably a methyl group, and at least four and most preferably all six of $R^5$ through $R^{10}$ are hydrogen atoms.

To produce the compounds of Formula (D) above, the benzoindenes (Formula (C) above) are deprotonated with a strong base such as butyllithium and reacted with a suitable silicon, germanium or tin reactant, which can be depicted by the formula $R^{11}R^{12}M^1X_2$ where X is a halogen atom (preferably a chlorine or bromine atom) and $M^1$, $R^{11}$ and $R^{12}$ are as described above. In a particularly preferred embodiment of this invention these operations are conveniently conducted in a dialkyl ether medium, typically a lower alkyl ether such as diethyl ether, dipropyl ether, methyl tert-butyl ether, ethyl tert-butyl ether, methyl tert-amyl ether, or dibutyl ether, most preferably diethyl ether. Unlike the situation where tetrahydrofuran is used in this procedure, the use of a liquid dialkyl ether enables the bridged product to form a slurry which is easily separated from the liquid phase by such procedures as filtration, centrifugation or decantation. If an solvent such as tetrahydrofuran is used, it is likely that a oily product will be formed which is hard to handle and to separate cleanly without recourse to solvent exchanging and an excessive amount of washing. Thus use of a dialkyl ether such as diethyl ethyl has proven to greatly facilitate the separation and recovery of the bridged product, and accordingly makes this operation entirely feasible for use in large plant scale operations.

In still another embodiment, the bridged compound of Formula (D) above is transformed into a metallocene complex of the formula:

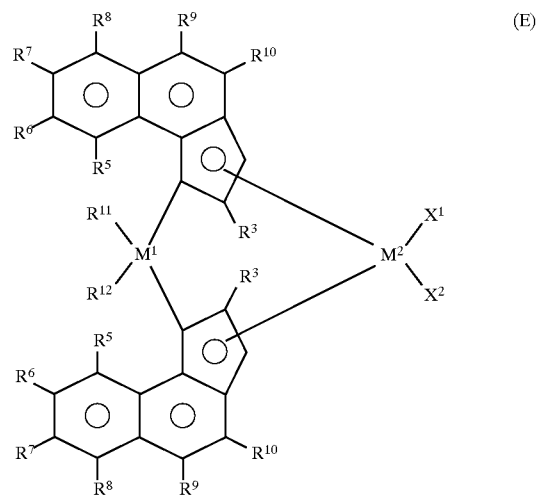

(E)

where $M^2$ is a group IV, V, or VI metal atom (i.e., Ti, Zr, Hf, V, Nb, Ta, Cr, Mo, or W); $X^1$ and $X^2$ are the same or different and each is a halogen atom (preferably a chlorine atom); and $M^1$, $R^3$ and $R^5$ through $R^{12}$ are as described above. Preferably $M^2$ is Ti, Zr or Hf, most preferably Zr; $X^1$ and $X^2$ are chlorine atoms; $M^1$ is a silicon atom; $R^{11}$ and $R^{12}$ are the same and are $C_1$ to $C_4$ alkyl groups, most preferably methyl or ethyl groups, $R^3$ is an alkyl group, most preferably a methyl group, and at least four and most preferably all six of $R^5$ through $R^{10}$ are hydrogen atoms.

Compounds of Formula (E) above are formed by deprotonating a bridged compound of Formula (D) above with a strong base such as butyllithium and reacting the deprotonated intermediate so formed with a suitable Group IV, V, or VI metal-containing reactant, such as a Group IV, V, or VI metal tetrahalide. The deprotonation is typically performed in an ether medium such as tetrahydrofuran or lower dialkyl ether. The metallation reaction can be conducted by adding the ether solution of the deprotonated intermediate portionwise to a preformed complex or mixture of the Group IV, V, or VI metal-containing reactant and an ether such as tetrahydrofuran in a hydrocarbon solvent such as toluene or xylenes or the like. However other solvent systems and modes of addition can be used.

A number of distinct advantages can be realized if the bridged metallocene of Formula (E) is produced by adding a chelate diamine adduct of the Group IV, V or VI metal tetrahalide to a solution or slurry of a deprotonated bridged compound of Formula (D) above, such as a dilithium or disodium derivative thereof. Such a procedure, when properly carried out, results in improved filterability of the reaction mixture, higher yields of product of formula (E), and product having higher ratios of racemic isomers to meso forms, as compared to the reverse addition of such reactants such as shown in U. S. Pat. No. 5,556,997.

Indeed, the advantages of this embodiment may be realized not only with dilithium or disodium derivatives of silicon-, germanium- or tin-bridged complexes depicted in Formula (D) but in addition, with dilithium or disodium derivatives of silicon-, germanium- or tin-bridged complexes analogous to those depicted in Formula (D) having other cyclopentadienyl moieties regardless of whether the moieties are composed of bridged single rings (e.g., cyclopentadienyl and hydrocarbyl-substituted cyclopentadienyl moieties) or bridged fused rings (e.g., indenyl, hydrocarbyl-substituted indenyl, fluorenyl, or hydrocarbyl-substituted fluorenyl moieties), and regardless of whether the two bridged cyclopentadienyl moieties are the same or are different from each other. Thus in this aspect of the invention dilithium or disodium derivatives of silicon-, germanium- or tin-bridged cyclopentadienyl-moiety-containing compounds having 5 to about 75 carbon atoms in the molecule can be used as the ligand. Examples of such ligands are given, for example, in U.S. Pat. Nos. 5,017,714; 5,329,033; 5,455,365; 5,455,366; and 5,541,350.

The chelate diamine adduct of a Group IV, V, or VI metal tetrahalide can be formed from such amines as N,N,N',N'-tetramethyldiaminomethane, N,N,N',N'-tetraethyldiaminomethane, N,N'-diethyl-N,N'-dimethyldiaminomethane, N,N,N',N'-tetramethylethylenediamine, N,N,N',N'-tetraethylethylenediamine, N,N'-diethyl-N,N'-dimethylethylenediamine, and like diamines capable of forming an adduct with such metal tetrahalides. The preferred diamine is N,N,N',N'-tetramethylethylenediamine.

Various compounds of Formula (E) are useful as components for catalyst systems for producing polyolefins such as polyethylene and polypropylene.

Examples 1–4 illustrate preferred procedures for conducting the overall sequence of steps that can be employed in the practice of this invention. Examples 5–7 illustrate preferred procedures for transforming the dilithium or disodium derivatives of silicon-, germanium- or tin-bridged cyclopentadienyl-moiety-containing compounds into the bridged metallocenes by addition thereto of the chelate diamine adduct of the Group IV, V, or VI metal tetrahalide pursuant to this invention. Examples 8–10, which show procedures that can be used in the overall sequence of reactions for effecting the same transformation, highlight the dramatic superiority and advantages of the preferred procedures illustrated in Examples 5–7. Unless otherwise specified, all percentages in the Example are by weight. It is to be clearly understood that Examples 1–7 are for the purposes of illustrating current best modes for carrying out the operations. None of the Examples is intended to limit, and should not be construed as limiting, the invention to the specific procedures set forth therein.

EXAMPLE 1

Preparation of 2-Methyl-4,5-benzoindanone

A slurry of 577 g (4.322 mol) $AlCl_3$ in 250 mL of methylene chloride was cooled to 5° C. To the slurry 372 g (1.618 mol) of 2-bromoisobutyryl bromide was added over 0.75 hour. After stirring for 0.5 hour, a solution of 207 g (1.616 mol) of naphthalene in 500 mL of methylene chloride was added at 5° C. over 1.5 hour. During the addition any HCl/HBr gas evolved overhead was scrubbed with a caustic solution. The resulting mixture was stirred for 0.5 hour at 5° C. and 1 hour at room temperature. The reaction slurry was then transferred to 2 to 3 liters of ice/water in a separate flask with agitation. HCl/HBr gas formed during the hydrolysis was scrubbed by a caustic solution. The organic phase (lower layer) of the hydrolyzed mixture was separated and saved. The upper aqueous layer was extracted once with 500 mL of methylene chloride. The combined organic phase and extract were washed with water (2×, 500 mL each) and the solvent was removed in vacuo to obtain crude product as a brown oil. The brown oil was flashed under 5 mm Hg vacuum and 158°–160° C. head temperature (or 170°–210° C. pot temperature) to collect 276 g (87% yield) of product as an orange oil. NMR analysis of the oil confirmed it was 2-methyl4,5-benzoindanone; GC analysis of the oil indicated it was 96% pure.

EXAMPLE 2

Preparation of 2-Methyl-4,5-benzoindanol and Conversion to 2-Methyl-4,5-benzoindene A solution of 2-methyl-4,5-benzoindanone (276 g, 1.408 mol) dissolved in 570 mL of THF and 570 mL of methanol was cooled to 5° C., and solid $NaBH_4$ (28 g, 0.74 mol) was added in portions to the solution over 45 minutes. After stirring for one hour at 5° C. and another hour at room temperature, the reaction mixture was quenched with 570 mL of water and followed by 60 mL of concentrated HCl (to bring the pH of the mixture to 2). The alcohols (2-methyl-4,5-benzoindanols) formed were extracted with toluene (2×, 500 mL each) and the combined extracts were washed with water (2×, 300 mL). The THF/methanol solvent in the toluene extract was distilled off under atmospheric pressure. When the pot temperature reached –113° C., the distillation was stopped and the mixture was cooled. Once the pot temperature was cooled down to about 80° C., 0.15 g of p-toluenesulfonic acid monohydrate was added, and the mixture was heated up again for one more hour to azeotrope off water (25 mL theory). After the azeotropic distillation was completed, all the toluene solvent in the mixture was removed under vacuum. 2-Methyl-4,5-benzoindene (254 g, 100% yield) was obtained as a brown oil. Analysis by NMR and GC confirmed the structure of the product and its purity was more than 95%.

EXAMPLE 3

Preparation of Dimethylsilylbis(2-methyl-4,5-benzoindene)

A solution of 567 mL (1.423 mol) of BuLi solution (2.5M in hexanes) was added at room temperature over 1.5 hour to a solution of 256 g (1.422 mol) of 2-methyl-4,5-benzoindene in one liter of dry diethyl ether. The mixture was allowed to reflux (39°–43° C.) during the addition. After the addition the mixture was heated at reflux for one hour and then cooled. At room temperature 92 g (0.7132 mol) of dichlorodimethylsilane was added to the pot over a period of 1.5 hours. The resulting mixture was stirred at room temperature overnight to form a slurry. Next morning 400 mL of ether was distilled off from the mixture and the slurry in the pot was cooled to 10° C. The precipitated dimethylsilylbis(2-methyl-4,5-benzoindene) and LiCl solids were filtered, and the cake was successively washed with ether (2×, 100 mL each), aqueous methanol (2×, 100 mL methanol+100 mL water, each) and followed by acetone (2×, 50 mL each). The cake was dried under 5 mm Hg/50° C. to thoroughly remove all methanol/ water to give 178 g (60% yield) of dimethylsilylbis(2-methyl-4,5-benzoindene) as tan-colored solids. The structure and purity of this product were confirmed by NMR analysis.

EXAMPLE 4

Preparation of Dimethylsilylbis(2-methyl-4,5-benzoindenyl)zirconium Dichloride

Dimethylsilylbis(2-methyl-4,5-benzoindene) (100.27 g, 0.241 mol) was partially dissolved in 300 mL of THF. This slurry was cooled to 0° C. and then two equivalents of n-BuLi (193 mL of 2.5M in hexanes; 0.48 mol) were added dropwise. A clear, amber solution of the dilithium derivative of the silyl-bridged reactant formed. After the addition was complete, the reaction mixture was allowed to warm to room temperature.

In a second flask, $ZrCl_4$ (56.8 g; 0.244 mol) was slurred in 500 mL of anhydrous toluene. THF (70 g; 0.97 mol) was added to this slurry to form the complex, $ZrCl_4(THF)_2$. The reaction was stirred overnight and then the solution of the dilithium derivative was added dropwise to the $ZrCl_4(THF)_2$ slurry over 75 minutes. An orange-yellow slurry formed. After 2 hours, the reaction mixture was heated in an oil bath and 350 mL of solvent were flash distilled. A vacuum was applied and an additional 450 mL of volatiles were removed. The slurry was stirred for 3 hours and then the solids were isolated by filtration on a coarse frit. The solids were washed with 20 mL of toluene, 40 mL of hexanes and then dried in vacuo. The yield of yellow solid was 100.3 grams. A $^1H$ NMR showed the metallocene was present in a rac/meso ratio of 1:1.

The crude product was slurried in 900 mL of anhydrous THF and heated to reflux overnight. The slurry was cooled to room temperature and filtered on a coarse frit. The yellow solids were washed with 35 mL of THF and dried in vacuo. The dried weight of dimethylsilylbis(2-methyl-4,5-benzoindenyl)zirconium dichloride was 41.4 grams (30% yield based on the initial silyl-bridged reactant). $^1H$ NMR determined the rac/meso ratio to be greater than 99:1.

EXAMPLE 5

Preparation of Dimethylsilylbis(2-methyl-4,5-benzoindenyl)zirconium Dichloride

In a dry box, 12 g of THF and $ZrCl_4$ (2.33 g; 10 mmol) were quickly mixed in a 50 mL flask (while the temperature increased from 22° C. to 38° C. due to the heat of ether adduct formation). The resultant white slurry was stirred at about 30° C. for 2.5 hours. N,N,N',N'-tetramethylethylene diamine (TMEDA, 0.85 g; 7.3 mmol) was added (in an approximately 5-minute period) and a white solid adduct dissolved to form a solution. After stirring at about 27° C. for approximately 10 minutes, the diamine adduct solution was used for reaction with the dilithium derivative of the silyl-bridged reactant as now to be described.

To a second 50 mL flask, THF (18 g) was added to dissolve 5.72 g of the dilithium derivative of dimethylsilylbis(2-methyl-4,5-benzoindene).$(THF/Et_2O)_2$ powder (72.2% normalized "$Li_2LIG$"; approximately 9.6 mmoles), containing ca. 2.7 wt % of the corresponding monolithium derivative ("LiLIG") as an impurity, ca. 23.6% THF and ca. 1.5% $Et_2O$. $Et_2O$ (6 g) was added. The above $ZrCl_4$-diamine adduct solution was added to this solution during a period of about 7 minutes while the temperature increased from 26° C. to 30° C. Additional THF (0.5 g) was used to wash the contents of the first flask into the mixture in the second flask. The reaction mass was stirred at about 30° C. for about 21 hours and then the reaction mass was heated up to 60° C. to strip 5.2 g of $Et_2O$/THF off before cooling the mixture down to 24° C. The slurry was easily filtered (under ca. 15 inches of Hg vacuum) and the wet cake was washed with 3 g THF. 3.42 Grams (ca. 59.4% recovery) of dried yellow powder were obtained which $^1H$ NMR indicated to contain 91.4% (normalized) racemic dimethylsilylbis(2-methyl-4,5-benzoindenyl)zirconium dichloride, 3.8% of the meso form, and 4.8% THF, and thus a racemic/meso ratio of 96/4.

EXAMPLE 6

Preparation of Dimethylsilylbis(2-methyl-4 5-benzoindenyl)zirconium Dichloride

THF (12.36 g) and $ZrCl_4$ (2.40 g; 10.3 mmol) were mixed in a 50 mL flask (while the temperature increased from 23° C. to 38° C.). After stirring at about 30° C. for about one hour, TMEDA (0.88 g; 7.6 mmol) was added into the white slurry over a 5-minute period to obtain a solution of the $ZrCl_4$-diamine adduct. This solution was added in about a 7-minute period to a solution (31.88 g) containing about 4.28 g $Li_2LIG$ (about 10 mmol), 7.3 g $Et_2O$, 20.1 g THF, 0.15 g (about 0.36 mmoles) LiLIG, and 0.04 g hexane (the last two of which were undesired impurities) at temperatures ranging from 25° to 30° C. Additional THF (0.5 g) was used for rinsing the contents of the first flask into the second flask. The reaction mass was stirred at ca. 30° C. for ca. 19.5 hours. Then the mixture was heated to 60° C. to strip off 7.81 g of $Et_2O$ and THF. After cooling to 24° C. and removal of a sample (0.8 g), the slurry was easily filtered. The wet cake (5.97 g) was treated with 7 g THF on the filter (for further removal of LiCl) at ambient temperature for 2 hours. Then the wet cake was filtered, washed with 3 g THF and then with 2 g methylene dichloride ($MeCl_2$), further treated twice with 4 g $MeCl_2$ for ca. 1 hour each time, and then dried to leave 3.06 g of a purified, nice yellow product which by NMR contained 95.1% (normalized) racemic dimethylsilylbis(2-methyl-4,5-benzoindenyl)zirconium dichloride, 1.4% of the meso form, 1.2% THF, and 2.3% $MeCl_2$. Thus NMR indicated the racemic/meso ratio was 98.5/1.5. ICP indicated the product contained 14.6% Zr and 655 ppm Li (ca. 0.4% LiCl). The recovery was ca. 53.1% (or ca. 55.1% including the 0.8 g sample). Analysis of the filtrates: The total THF filtrate (38.1 g) showed 0.45% (normalized) racemic dimethylsilylbis(2-methyl-4,5-benzoindenyl)zirconium dichloride, 0.38% of the meso form (rac/meso=54/46), 2.1% TMEDA, 7.9% $Et_2O$ and 89.1% THF. The total $MeCl_2$ filtrate (5.51 g) showed 0.8% racemic dimethylsilylbis(2-methyl-4,5-benzoindenyl)zirconium dichloride, 0.2% meso form, 0.2% $Et_2O$, 20.6% THF and 78.2% $MeCl_2$.)

EXAMPLE 7

Preparation of Dimethylsilylbis(2-methyl-4,5-benzoindenyl)zirconium Dichloride $ZrCl_4$ (2.33 g; 10 mmol) and THF (12 g) were quickly mixed. TMEDA (1.16 g; 10 mmol) was added to the slurry to produce a thin slurry. The resultant slurry was added over a 7-minute period to a solution at ca. 30° C. formed from 5.72 g of $Li_2LIG.(THF/Et_2O)_2$ solid and 15 g of THF, and 0.5 g of THF was used for rinsing product from the first flask into the second. The reaction mass was stirred at ca. 28° C.

for 20 hours and heated to and caused to ride at 50° C. for 1.2 hours. After the reaction mass was cooled down, a slurry sample (0.68 g) was taken, and it had an estimated content of 8.7% racemic dimethylsilylbis(2-methyl-4,5-benzoindenyl)zirconium dichloride, 0.9% meso form (racemic/meso=90.6/9.4), 3.3% TMEDA, 86.7% THF and 0.4% $Et_2O$. The filtration was relatively easy, and the wet cake was washed with 6 g THF and dried to give 2.48 g (ca. 43% recovery) of product having 93.9% (normalized) racemic dimethylsilylbis(2-methyl-4,5-benzoindenyl)zirconium dichloride, 2.8% of the meso form, and 3.2% THF. The total filtrate (31.2 g) contained 1.1% racemic dimethylsilylbis(2-methyl-4,5-benzoindenyl)zirconium dichloride, 0.8 wt % of the meso product (rac/meso=58/42), 0.3% $Et_2O$, 4% TMEDA and 93.8% THF.

EXAMPLE 8

Preparation of Dimethylsilylbis(2-methyl-4,5-benzoindenyl)zirconium Dichloride

In this run, the $ZrCl_4$ was added to the dilithium ligand as the $ZrCl_4 \cdot (THF)_2$ adduct; no chelating diamine was used. $ZrCl_4$ (2.80 g; 12 mmol) and 15 g of THF were quickly mixed and stirred for 1 hour resulting in a white slurry. The slurry was added to a 22.8 g solution composed of 20.9% $Li_2LIG.(THF/Et_2O)_2$, (ca. 11.1 mmol), 78% THF, 0.1% LiLIG and 1.1% pentane at about 25°–30° C. over a 20-minute period using an additional 3 g of THF for wash. After 21-hour riding at ambient temperature, the slurry was heated up to 60° C. for 4 hours (to improve the filtration). Two slurry samples (0.5 & 0.4 g) were taken before and after the heatup and had 6.2 & 6.1% (normalized) racemic dimethylsilylbis(2-methyl-4,5-benzoindenyl)zirconium dichloride, and 0.6 & 0.8% of the meso product (rac/meso= 91.2/8.8 & 88.4/11.6), respectively. The filtration was slow (about 1.5 hours or about 5 to 10 times slower than when operating as in Examples 5–7 above). After the product was washed with 6 g of THF and dried, 2.36 g of racemic dimethylsilylbis(2-methyl-4,5-benzoindenyl)zirconium dichloride product were obtained (ca. 34.1% recovery) with 89.5% (normalized) racemic dimethylsilylbis(2-methyl-4,5-benzoindenyl)zirconium dichloride, 0.9 wt % of the meso form, and 3.7 wt % THF (likely adducted). The filtrate (35.3 g) contained by analysis 1.5% racemic dimethylsilylbis(2-methyl-4,5-benzoindenyl)zirconium dichloride, 1.2% of the meso product (rac/meso=56/44), 96.9% THF and 0.4% pentane.

EXAMPLE 9

Preparation of Dimethylsilylbis(2-methyl-4,5-benzoindenyl)zirconium Dichloride

In this run the reverse addition was used, i.e., the dilithium ligand was added to the $ZrCl_4$-chelate diamine adduct. Thus $ZrCl_4$ (2.80 g; 12 mmol) and 15 g of THF were quickly mixed. TMEDA (0.39 g; 3.4 mmol) was added to obtain a solution. After this was stirred for 20 minutes, a solution formed from 6.87 g of $Li_2LIG$ solid (ca. 12 mmol) and 15 g of THF was fed with a dropping funnel to the above $ZrCl_4$-TMEDA solution at ca. 30° C. for 20 minutes. After this mixture was stirred at ca. 30° C. for 21 hours, a slurry sample (0.52 g) showed by analysis 4.7% (normalized) racemic dimethylsilylbis(2-methyl-4,5-benzoindenyl) zirconium dichloride, 0.75% of the meso product (rac/meso=86/14), 93.3% THF, 1.0 t % $Et_2O$ and 0.3 wt % TMEDA, which indicated that the reaction yield of racemic dimethylsilylbis(2-methyl-4,5-benzoindenyl)zirconium dichloride was much lower. The slurry was heated up to and caused to ride at 60° C. for 1.3 hours and was then cooled down. The workup was terminated because the filtration was very slow.

EXAMPLE 10

Preparation of Dimethylsilylbis(2-methyl-4,5-benzoindenyl)zirconium Dichloride

Again a reverse addition was used but in this case, the reactants were used as slurries. Thus, $ZrCl_4$ (1.40 g; 6 mmol) and 10 g of $Et_2O$ were quickly mixed. THF (1.3 g; 18 mmol) and TMEDA (0.2 g; 1.7 mmol) were added yielding a white slurry. After stirring for 20 minutes, 3.44 g of $Li_2LIG.(THF/Et_2O)_2$ and 10 g of $Et_2O$ were added in about 5 minutes. The resultant slurry was stirred at about 30° C. for 18 hours. A sample (0.49 g) had 6.6% (normalized) racemic dimethylsilylbis(2-methyl-4,5-benzoindenyl)-zirconium dichloride, and 6.0% of the meso product (rac/meso=52.6/47.4). THF (15 g) was added to the mixture and the reaction mass was heated up to 50° C. and some $Et_2O/THF$ was stripped off. After the reaction mass cooled down, the slurry was easily filtered. However, when 10 g of THF were added for purification (e.g. for removal of LiCl and the meso product), the filtration became very slow. Finally, 3.68 g of yellow powder were obtained which by analysis had 48.3% (normalized) racemic dimethylsilylbis(2-methyl-4,5-benzoindenyl)zirconium dichloride, 42.6% of the meso form (rac/meso=63.1/46.9), 8.8% THF and 0.9% $Et_2O$ (likely both adducted).

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended, formed in situ, or mixed with one or more other substances, components and/or ingredients in accordance with the present disclosure. The fact that the substance, component or ingredient may have lost its original identity through a chemical reaction or transformation during the course of such contacting, blending, formation in situ, or mixing operations is thus wholly immaterial for an accurate understanding and appreciation of this disclosure and the claims thereof.

Each and every patent or other publication referred to in any portion of this specification is incorporated in toto into this disclosure by reference for all purposes, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for preparing a metallocene which comprises adding a diamine adduct of a Group IV, V, or VI metal tetrahalide to:
   (a) a solution or slurry formed from a deprotonated silicon-, germanium- or tin-containing ligand and an organic liquid medium; and/or
   (b) a solution or slurry in an organic liquid medium in which a deprotonated silicon-, germanium- or tin-containing ligand is formed; and/or
   (3) an organic liquid medium containing a solution or slurry of said deprotonated silicon-, germanium- or tin-containing complex in whatever chemical form it exists while in said solution or slurry;
so as to form a metallocene.

2. A process according to claim 1 wherein said adduct is added as:
   (a) a solution or slurry formed from said adduct and an organic liquid medium; and/or
   (b) a solution or slurry in an organic liquid medium in which said adduct is formed; and/or
   (c) an organic liquid medium containing a solution or slurry of said adduct in whatever chemical form it exists while in said solution or slurry.

3. A process according to claim 1 wherein the metal of said adduct is a Group IV metal.

4. A process according to claim 1 wherein the metal tetrahalide of said adduct is a Group IV metal tetrachloride or Group IV metal tetrabromide, or mixture thereof.

5. A process according to claim 1 wherein said ligand is a dilithium or disodium derivative of said ligand.

6. A process according to claim 1 wherein said ligand is a dilithium derivative of said ligand.

7. A process according to claim 2 wherein the metal tetrahalide of said adduct is a Group IV, V, or VI metal tetrachloride or a Group IV, V, or VI metal tetrabromide, and wherein said ligand is a bridged ligand formed by deprotonating 4,5-benzoindene or a hydrocarbyl-substituted 4,5-benzoindene with a strong lithium base and reacting the resultant deprotonated intermediate with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly(oxyalkylene) group containing up to about 100 carbon atoms; $M^1$ is a silicon, germanium or tin atom; and X is a halogen atom; such that a silicon-, germanium- or tin-bridged complex of the 4,5-benzoindene is formed.

8. A process according to claim 2 wherein the metal tetrahalide of said adduct is a Group IV metal tetrachloride or Group IV metal tetrabromide, or mixture thereof, and wherein said ligand is a dilithium derivative of said ligand.

9. A process according to claim 8 wherein said ligand is a deprotonated dialkylsilylbis(2-alkyl-4,5-benzoindene or an etherate thereof in which the ether(s) thereof is/are linear or cyclic, or in which the ethers are a combination of linear and cyclic ethers.

10. A process according to claim 8 wherein said ligand is a dilithium derivative of dimethylsilylbis(2-methyl-4,5-benzoindene or an etherate thereof.

11. A process according to claim 10 wherein the metal tetrahalide of said adduct is a Group IV metal tetrachloride.

12. A process which comprises:
   1) mixing together at least one of each of the following: (a) a 4,5-benzoindanone, (b) an alkali or alkaline earth metal borohydride or alkali or alkaline earth metal aluminum hydride, and (c) a hydroxyl-containing compound capable of interacting with (b) to serve as a hydrogen source, under reaction conditions causing a 4,5-benzoindanol to be formed;
   2) catalytically dehydrating said 4,5-benzoindanol using a arylsulfonic acid catalyst to thereby form a 4,5-benzoindene;
   3) deprotonating said 4,5-benzoindene with a strong base and reacting the resultant deprotonated intermediate with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly(oxyalkylene) group containing up to about 100 carbon atoms; $M^1$ is a silicon, germanium or tin atom; and X is a halogen atom; such that a silicon-, germanium- or tin-bridged complex of the 4,5-benzoindene is formed; and
   4) deprotonating said bridged complex with a strong base and adding a diamine adduct of a Group IV, V, or VI metal tetrahalide to:
      (A) a solution or slurry formed from said deprotonated silicon-, germanium- or tin-bridged complex and an organic liquid medium; and/or
      (B) a solution or slurry in an organic liquid medium in which said deprotonated silicon-, germanium- or tin-bridged complex is formed; and/or
      (C) an organic liquid medium containing a solution or slurry of said deprotonated silicon-, germanium- or tin-bridged complex in whatever chemical form it exists while in said solution or slurry;
so as to form a silicon-, germanium- or tin-bridged Group IV, V, or VI metal-containing metallocene.

13. A process according to claim 12 wherein $R^{11}$ and $R^{12}$ are the same and are $C_1$ to $C_4$ alkyl groups, wherein $M^1$ is a silicon atom, wherein X is a bromine or chlorine atom, and wherein the Group IV, V, or VI metal-containing reactant is a zirconium tetrahalide.

14. A process according to claim 13 wherein the mixture formed in 1) further includes at least one ether, wherein the 4,5-benzoindanone is a 2-alkyl-4,5-benzoindanone, wherein (b) is an alkali metal borohydride, wherein (c) is water or an alcohol, and wherein the zirconium tetrahalide is zirconium tetrachloride or zirconium tetrabromide.

15. A process according to claim 14 wherein the ether is at least predominately tetrahydrofuran, wherein the 2-alkyl-4,5-benzoindanone is a major amount of 2-methyl-4,5-benzoindan-1-one and a minor amount of 2-methyl-4,5-benzoindan-3-one, and wherein (b) is sodium borohydride.

16. A process according to claim 12 wherein the mixture formed in 1) further includes at least one ether, wherein the reaction in 1) is terminated by quenching the reaction mixture with water or an aqueous mixture, and wherein 4,5-benzoindanol formed in 1) is separated from ether and water prior to conducting the catalytic dehydration of 2).

17. A process according to claim 16 wherein the separation of 4,5-benzoindanol from the ether and water is effected by extracting the quenched reaction mixture with a liquid aromatic hydrocarbon having a higher boiling point or a higher initial boiling point than the ether, and distilling at least the ether from the resultant extract.

18. A process according to claim 13 wherein the mixture formed in 1) further includes at least one ether, wherein the 4,5-benzoindanone is a 2-alkyl-4,5-benzoindanone, wherein (b) is an alkali metal borohydride, wherein (c) is water or an alcohol, wherein the reaction in 1) is terminated by quenching the reaction mixture with water or an aqueous mixture, wherein a separation between the water and organic constituents of the reaction mixture is effected by extracting the quenched reaction mixture with a liquid hydrocarbon having a higher boiling point or a higher initial boiling point than the ether, and, if present, the alcohol, wherein said ether and, if present, said alcohol are distilled off to leave a liquid hydrocarbon solution of the 4,5-benzoindanol formed in 1), and wherein the catalytic dehydration of 2) is conducted without isolating the 4,5-benzoindanol from the liquid hydrocarbon solution.

19. A process according to claim 18 wherein the ether is at least predominately tetrahydrofuran, wherein the 2-alkyl-4,5-benzoindanone is a mixture of a major amount of 2-methyl-4,5-benzoindan-1-one and a minor amount of 2-methyl-4,5-benzoindan-3-one, and wherein (b) is sodium borohydride.

20. A process according to claim 19 wherein (c) is an alcohol and wherein the liquid hydrocarbon consists essentially of at least one mononuclear aromatic hydrocarbon capable of forming an azeotrope with water.

21. A process according to claim 12 wherein the strong base used in 3) and in 4) is a lithium alkyl.

22. A process which comprises (a) deprotonating a 4,5-benzoindene with a strong base and reacting the resultant deprotonated intermediate while dissolved in a liquid lower dialkyl ether with a reactant which in its original condition can be depicted by the formula $R^{11}R^{12}M^1X_2$ where $R^{11}$ and $R^{12}$ are the same or different and each is (i) a hydrocarbyl group containing up to about 18 carbon atoms or (ii) a hydrocarbyl(oxyalkylene) or hydrocarbylpoly(oxyalkylene) group containing up to about 100 carbon atoms; $M^1$ is a silicon, germanium or tin atom; and X is a halogen atom; such that a slurry of a silicon-, germanium- or tin-bridged complex of the 4,5-benzoindene is formed: (b) separating the solids from the liquid phase; and (c) adding a diamine adduct of a Group IV, V, or VI metal tetrahalide to:

(1) a solution or slurry formed from said deprotonated silicon-, germanium- or tin-containing complex and an organic liquid medium; and/or (2) a solution or slurry in an organic liquid medium in which said deprotonated silicon-, germanium- or tin-containing complex is formed; and/or (3) an organic liquid medium containing a solution or slurry of said deprotonated silicon-, germanium- or tin-containing complex in whatever chemical form it exists while in said solution or slurry;

so as to form a silicon-, germanium- or tin-bridged Group IV, V, or VI metal-containing metallocene.

23. A process according to claim 22 wherein the 4,5-benzoindene is a 2-alkyl-4,5-benzoindene, wherein the strong base is a lithium alkyl and wherein said reactant is a dialkyldihalosilane.

24. A process according to claim 22 wherein the 4,5-benzoindene is a 2-alkyl-4,5-benzoindene, and wherein said reactant is a dialkyldihalosilane in which the alkyl groups contain no more than 4 carbon atoms each.

25. A process according to claim 22 wherein the 4,5-benzoindene is a 2-alkyl-4,5-benzoindene, wherein the strong base is a lithium alkyl, wherein said reactant is a dialkyldihalosilane, and wherein said solids are separated from the liquid phase by filtration.

26. A process according to claim 22 wherein the 4,5-benzoindene is 2-methyl-4,5-benzoindene, wherein the strong base is butyllithium, wherein said ether is diethyl ether, wherein said reactant is dichlorodimethylsilane, and wherein said solids are separated from the liquid phase by filtration.

27. A process according to claim 22 wherein said adduct is added as:

(1) a solution or slurry formed from said adduct and an organic liquid medium; and/or (2) a solution or slurry in an organic liquid medium in which said adduct is formed; and/or (3) an organic liquid medium containing a solution or slurry of said adduct in whatever chemical form it exists while in said solution or slurry.

28. A process according to claim 22 wherein the metal of said adduct is a Group IV metal.

29. A process according to claim 27 wherein the metal tetrahalide of said adduct is a Group IV metal tetrachloride or Group IV metal tetrabromide, or mixture thereof.

30. A process according to claim 29 wherein said ligand is a dilithium or disodium derivative of said ligand.

* * * * *